United States Patent [19]
Jarrell

[11] Patent Number: 5,230,777
[45] Date of Patent: Jul. 27, 1993

[54] APPARATUS FOR PRODUCING FUEL AND CARBON BLACK FROM RUBBER TIRES

[76] Inventor: James Jarrell, 62 Hickory Hills Dr., Dexter, Mo. 63841

[21] Appl. No.: 807,432

[22] Filed: Dec. 13, 1991

[51] Int. Cl.$^5$ ............................................. C10B 1/02
[52] U.S. Cl. ....................................... 202/97; 202/105; 202/110; 202/113; 202/150; 202/266
[58] Field of Search ................. 202/97, 98, 105, 110, 202/113, 150, 266; 201/35

[56] References Cited

U.S. PATENT DOCUMENTS

| | | | |
|---|---|---|---|
| 871,313 | 11/1907 | Willink | 202/97 |
| 980,509 | 1/1911 | Gautier | 202/97 |
| 1,846,363 | 2/1932 | Schisler | |
| 1,898,326 | 2/1933 | Wahlstrom | 202/97 |
| 3,823,224 | 7/1974 | Laman et al. | |
| 3,875,077 | 4/1975 | Sanga | |
| 3,996,022 | 12/1976 | Larsen | |
| 4,029,550 | 6/1977 | Mitsui et al. | |
| 4,030,984 | 6/1977 | Chambers | |
| 4,038,100 | 7/1977 | Haberman | |
| 4,084,521 | 4/1978 | Herbold et al. | |
| 4,203,804 | 5/1980 | Janning et al. | |
| 4,235,676 | 11/1980 | Chambers | |
| 4,250,158 | 2/1981 | Solbakken et al. | |
| 4,284,616 | 8/1981 | Solbakken et al. | |
| 4,300,985 | 11/1981 | Gagneraud | |
| 4,384,151 | 5/1983 | Audibert et al. | |
| 4,401,513 | 8/1983 | Brewer | |
| 4,402,791 | 9/1983 | Brewer | |
| 4,452,154 | 6/1984 | Kono et al. | |
| 4,506,034 | 3/1985 | Munih | |
| 4,507,174 | 3/1985 | Kutrieb | |
| 4,552,621 | 11/1985 | Lyakhevich et al. | |
| 4,565,138 | 1/1986 | Ueda et al. | |
| 4,588,477 | 5/1986 | Habib | |
| 4,642,401 | 2/1987 | Coenen et al. | |
| 4,647,443 | 3/1987 | Apffel | |
| 4,648,328 | 3/1987 | Keough | |
| 4,686,007 | 8/1987 | Lyakhevich et al. | |
| 4,686,008 | 8/1987 | Gibson | |
| 4,740,270 | 4/1988 | Roy | |
| 4,746,406 | 5/1988 | Timmann | |
| 4,839,151 | 6/1989 | Apffel | |
| 4,900,401 | 2/1990 | Horton | |
| 5,082,534 | 1/1992 | Breu | 202/113 |

FOREIGN PATENT DOCUMENTS 324668 7/1989 European Pat. Off. ............ 202/113
WO92/01767 2/1992 PCT Int'l Appl.

OTHER PUBLICATIONS

Rubber Technology, Second Edition, Edited by Maurice Morton pp. 496–514.

*Primary Examiner*—Joye L. Woodard
*Attorney, Agent, or Firm*—Bryan Cave

[57] ABSTRACT

A method and apparatus for producing fuel and carbon black from rubber are disclosed. The method and apparatus produce a liquid fuel that is low in sulfur content, gaseous hydrocarbons, and solid carbonaceous materials from used rubber tires. Rubber is heated under negative pressures in the presence of a minimal amount of oxygen. The methods and apparatus of the present invention also produce little air emissions and conserve energy.

4 Claims, 2 Drawing Sheets

APPARATUS FOR PRODUCING FUEL AND CARBON BLACK FROM RUBBER TIRES

FIELD OF THE INVENTION

The present invention relates generally to the conversion of rubber into fuels and other useful products. More particularly, the present invention relates to a novel method and apparatus for obtaining low sulfur liquid fuels, gaseous hydrocarbons, and solid carbonaceous materials, from used rubber tires. In preferred embodiments the process operates in a closed loop, batch apparatus that allows only minimal amounts of air leakage and create little secondary waste and air emissions.

BACKGROUND

Throughout the world, passenger cars and trucks wear out millions of tires every year. Unfortunately, it is difficult to dispose of the used tires. Burning is usually prohibited because of air pollution concerns, and burying can lead to landfill contamination. As a result, used tires tend to accumulate creating eyesores and environmental hazards.

A particularly desirable way to dispose of used tires is to recover hydrocarbons and carbonaceous materials from the tires. The hydrocarbons can be used as fuel sources replacing expensive petroleum products, and the solid carbonaceous products have many end uses.

The conversion of rubber into fuels is generally known. Roy (U.S. Pat. No. 4,740,270) relates to the vacuum pyrolysis of tires at a temperature of from about 360-415 degrees centigrade (hereinafter "°C") under pressures of less than about 725 millimeters of mercury (hereinafter "mm Hg") absolute. Solbakken et al. (U.S. Pat. No. 4,284,616) relates to the pyrolysis of tire fragments at approximately 454°-566° C. for 30 to 10 minutes under an oxygen limited, hydrocarbons vapor atmosphere at about 310-1138 mm Hg absolute. Solbakken et al. (U.S. Pat. No. 4,250,158) relates to the pyrolysis of tire fragments at approximately 454° C. for 5 to 10 minutes under an oxygen limited, hydrocarbon vapor atmosphere at about 310-621 mm Hg absolute. Chambers (U.S. Pat. No. 4,235,676) relates to the heating of shredded rubber tires at a temperature of 427°-816° C. in the absence of air and/or oxygen, at a pressure of from about 608-658 mm Hg absolute. Herbold et al. (U.S. Pat. No. 4,084,521) relates to the pyrolysis of waste products containing hydrocarbons by heating the material at a sub-atmospheric pressure and a preferable temperature of between 400°-800° C.

The processes and apparatus of the prior art have several disadvantages. They are generally not capable of producing liquid hydrocarbons having low sulfur content. As a result, the liquid hydrocarbons produced by such processes and apparatus create high sulfur emissions when burned. Alternatively, the liquid fuels must be further processed to remove sulfur before being used as fuels.

The existing processes and apparatus also involve significant fire and explosion risk due to the presence of oxygen during preheating or pyrolysis. Other drawbacks of the processes and apparatus of the prior art include the fact that they often produce high levels of emissions and produce secondary wastes. Some processes and apparatus also use dangerous catalysts.

A process and apparatus has now been developed that overcomes the above-noted problems and also has numerous other advantages that will be apparent to those skilled in the art.

SUMMARY OF THE INVENTION

A process and apparatus have now been developed that overcome the above-noted problems and also have numerous other advantages that will be apparent to those skilled in the art.

Broadly, the process of the present invention produces liquid and gaseous hydrocarbons from rubber. The process comprises (a) heating rubber in at least one sealed reactor at a temperature of about 127°-440° C. under a pressure of about 25.4-759 mm Hg absolute for a reaction time sufficient to cause the rubber to dissociate into a vapor phase and a solid phase; (b) removing at least some of the vapor phase from the reactor to produce a vapor stream; and (c) condensing at least some of the vapor stream to produce low sulfur liquid hydrocarbons and remaining gaseous hydrocarbons. In preferred embodiments the process further comprises the step of (d) processing the solid phase to produce a solid carbonaceous material. It is preferred to have a temperature range of about 400°-438° C., even more preferably 427°-432° C. Preferred pressure ranges are 404-607 mm Hg, more preferably 416-568 mm Hg. absolute. A preferred reaction time is about 2½-4 hours. Preferably the liquid hydrocarbon will have less than about 1.0 percent sulfur by weight, even more preferably less than about 0.5 or even 0.4 percent by weight sulfur. In other preferred embodiments the rubber comprises whole tires, produces minimal amounts of air pollution, and the amount of air entering the reactor is less than 0.5 weight percent as compared to all vapors and gases in the reactor.

Another aspect of the present invention concerns a batch process for producing liquid and gaseous hydrocarbons from rubber. This process comprises (a) heating rubber in a first sealed reactor at a temperature of about 127°-440° C. under a pressure of about 25.4-759 mm Hg absolute for a reaction time sufficient to cause the rubber to dissociate into a vapor phase and a solid phase, wherein said heating produces a warm exhaust; (b) removing at least some of the vapor phase from the reactor to produce a vapor stream; (c) condensing at least some of the vapor stream to produce low sulfur liquid hydrocarbons and remaining gaseous hydrocarbons;(d) preheating a second sealed reactor with the warm exhaust of step (a); and (e) after the reaction time of step (a) allowing heat to pass from the first reactor to the second reactor. In a preferred embodiment the heating is performed by at least one heating means and the process further comprises the step of (f) delivering at least some of the remaining gaseous hydrocarbons to the heating means to act as a fuel of the heating means.

Yet another aspect of the present invention is an apparatus for producing liquid and gaseous hydrocarbons and solid carbonaceous materials from rubber. The apparatus comprises (a) at least one reactor for holding the rubber, said reactor capable of withstanding internal temperatures of from about 127°-440° C. and internal pressures of from about 25.4-759 mm Hg absolute with minimal amounts of air leakage; (b) at least one heating means for heating the at least one sealed reactor to an internal temperature of from about 127°-440° C. and pressure reducing means for producing a pressure in the at least one reactor of from about 25.4-759 mm Hg absolute so that any rubber in the at least one sealed reactor dissociates into a vapor phase and a liquid phase; (c) means for withdrawing the vapor phase from the at least one reactor and delivering it to a condensing means; (d) condensing means for condensing at least some of the vapor phase to produce low sulfur liquid hydrocarbons and remaining gaseous hydrocarbons; and (e) processing means for processing the solid phase to produce solid carbonaceous materials. In preferred embodiments the means for withdrawing the vapor phase comprises at least two pipes in fluid communication with the reactor, and at least one pipe is configured above the vertical center of the reactors and at least one pipe is configured below the vertical center of the reactors. The apparatus will preferably comprise magnetic separators for removing steel from the solid phase and will use whole tires. The apparatus will preferably further comprise a (f) means for delivering at least some of the remaining gaseous hydrocarbons to the heating means to serve as a fuel. Even more preferred, the apparatus will further comprise (g) means for delivering the warm exhaust from the heating means to the reactors, so that the exhaust can heat or preheat the reactors.

Another aspect of the present invention is an apparatus comprising (a) two sealed reactors for holding rubber, said reactors capable of withstanding internal temperatures of from about 127°–440° C. and internal pressures of from about 25.4–759 mm Hg absolute with minimal amounts of air leakage; (b) valved pressure equalization means capable of equalizing the pressure between the two sealed reactors; (c) heating means for heating the two sealed reactors to an internal temperature of from about 127°–440° C. and pressure reducing means for producing a pressure in the two sealed reactors of from about 25.4–759 mm Hg so that any rubber in the at least one reactor dissociates into a vapor phase and a liquid phase; (d) means for withdrawing the vapor phase from the two reactors and delivering it to a condensing means; (e) condensing means for condensing at least some of the vapor phase to produce low sulfur liquid hydrocarbons and remaining gaseous hydrocarbons; and (f) processing means for processing the solid phase to produce solid carbonaceous materials.

The valve pressure equalization means will preferably comprise a valved pipe running between the two reactors that allows pressure equalization between the reactors when the valve is open and thereby allows heat to pass from one reactor to the other. The apparatus will preferably use whole rubber tires, and will further comprise (g) means for delivering at least some of the remaining gaseous hydrocarbons to the heating means to serve as a fuel for the heating means. The apparatus will preferably further comprise a means for delivering the warm exhaust from the heating means to the reactors to heat or preheat the reactors. In even more preferred embodiments, the apparatus produces minimal amounts of air pollution.

Another aspect of the present invention is the low sulfur liquid hydrocarbon preferably comprising less than 0.40 weight percent sulfur; the solid carbonaceous product preferably comprising less than 1.0 percent water; and the emulsion preferably comprising about 55 percent liquid hydrocarbon and about 45% solid carboneceous product; produced by the processes of the present invention. An even more preferred solid carbonaceous product comprises by weight about 0.5–1.5% water; 7.0–10.0 percent ash; and 86–92 percent carbon.

Other features and advantages of this invention will be apparent to those skilled in the art.

BRIEF DESCRIPTION OF THE DRAWING

To facilitate further discussion of the invention, the following drawing is provided in which.

Figure 1:
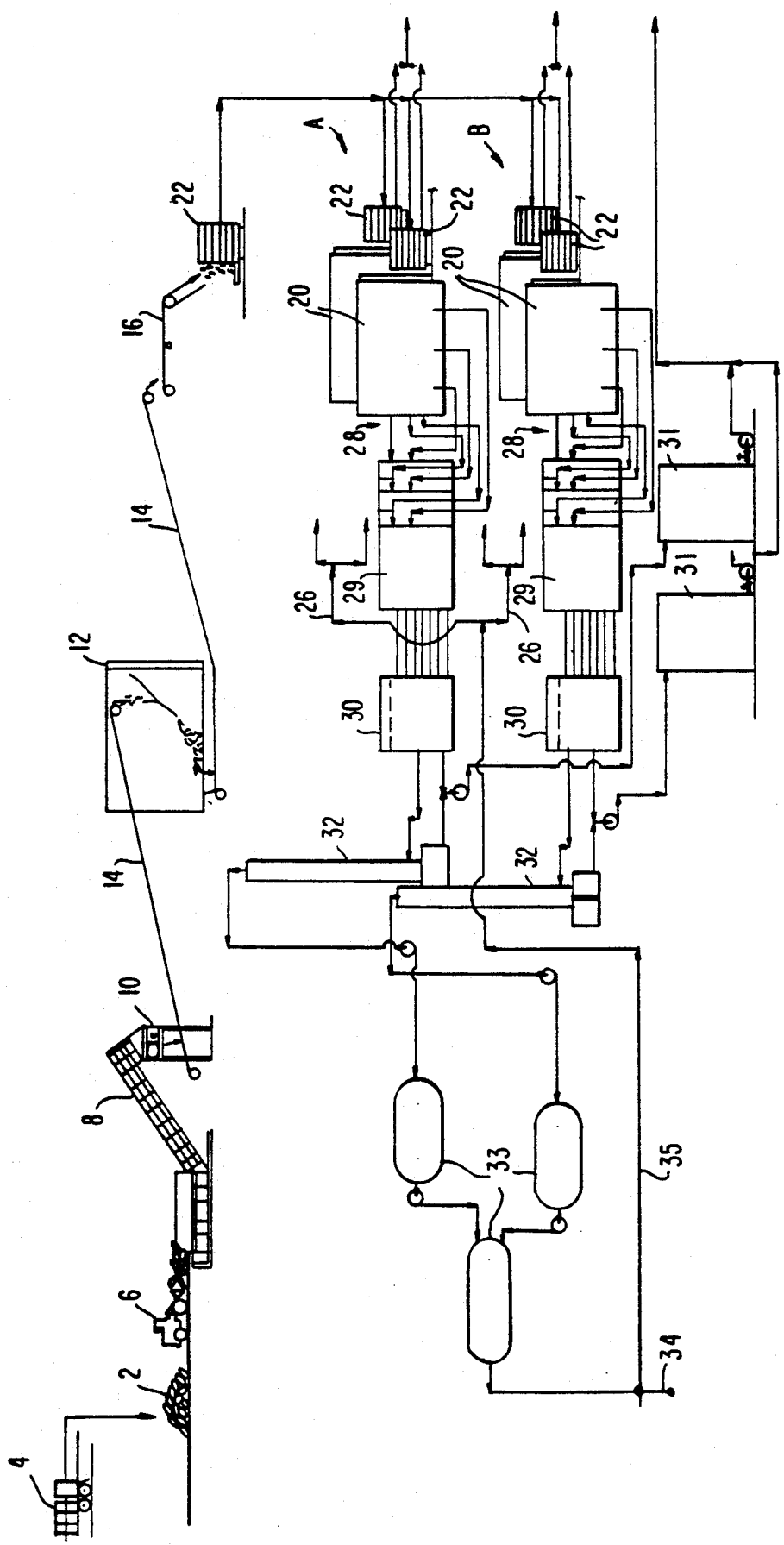
FIG. 1 is a schematic flow sheet illustrating a preferred embodiment of the apparatus of the present invention, in which two reaction trains are shown for processing rubber tires in accordance with the present invention.

The scope and content of the invention will be apparent from the following description of the preferred embodiments thereof, considered in conjunction with the drawing.

DETAILED DESCRIPTION OF THE INVENTION

With reference to FIG. 1, raw material in the form of used tires and scrap rubber 2 is brought to a receiving area, usually in semi-trailers 4. The waste tires and other scrap rubber may be removed from the semi-trailers by skid loaders 6 especially adapted to unload the materials. The receiving area may be enclosed and may be of any suitable configuration depending upon the capacity of the operation. A preferred receiving area is an enclosure that is approximately 30.5 meters (hereinafter "m")×30.5 m and has push walls that are 4.5 m high.

The used tires and other scrap rubber may be reduced in a reduction unit 10 before being processed. The tires and other scrap rubber 2 can be transported to the reduction unit 10 by any suitable means, such as a 152.5 centimeters (hereinafter "cm") wide apron conveyor 8 equipped with a variable speed drive set for 0–15 m per minute.

Uniformity of the tire and other scrap rubber pieces 2 is not required, and, for instance, whole tires can be used in the process and apparatus of the present invention. In fact, an advantage of the present invention is that a reduction step can be completely avoided. A reduction step usually requires costly equipment. However, it is sometimes preferable to reduce tires, typically into six non-uniform pieces, in order to more easily load the tires into the reactors 20.

The tires may be reduced by any reduction means known to those skilled in the art. A preferred tire reduction unit 10 is a shear/shredder. An especially preferred shredder is an American Pulverizer 72×52 Slow Speed Shear Mill and a La Bounty Shear with a maximum capacity of 2,200 tires per hour. The tires will generally have a bulk density of about 160 Kilograms per cubic meter (hereinafter "$Kg/m^3$") before reduction, and a bulk density of about 288 $Kg/m^3$ after reduction.

After reduction, the tire chips may be sent directly to the reactor(s) 20 of the present invention, or may be stored for later use. If storage is desired, a chipped tire conveyor 14 can transport the tire chips from the shredder discharge to an isolated chip storage area 12, and then from the storage area 12 to the reactor(s) 20. A preferred conveyor 14 for this purpose is a 152.5 cm wide unit with a speed of 45 m/minute.

The rubber 2 can be placed on at least one rack 22 in order to facilitate loading and unloading of the reactor(s) 20. The racks also tend to increase the reaction efficiency by distributing the rubber and therefore increasing reaction surface area. The racks may be of any suitable configuration depending upon the dimensions of the reactor(s) 20 to be used. A preferred rack configuration has six trays, with each tray capable of holding approximately 345.5 kilograms (hereinafter "Kg") of rubber. The rack trays are spaced on a vertical axis approximately 30.5 cm apart from each other.

The rubber may be weighed before being placed on a rack, preferably by a weigh belt 16. Each rack 22, once filled with rubber, is loaded into a reactor 20. The rack 22 can be loaded into the reactor 20 by any acceptable means, such as by a forklift.

As illustrated in FIG. 1, a preferred embodiment of the apparatus of the invention incorporates reaction trains A and B, each of which comprises a pair of reactors 20 and their associated gas and liquid processing equipment.

Figure 2:
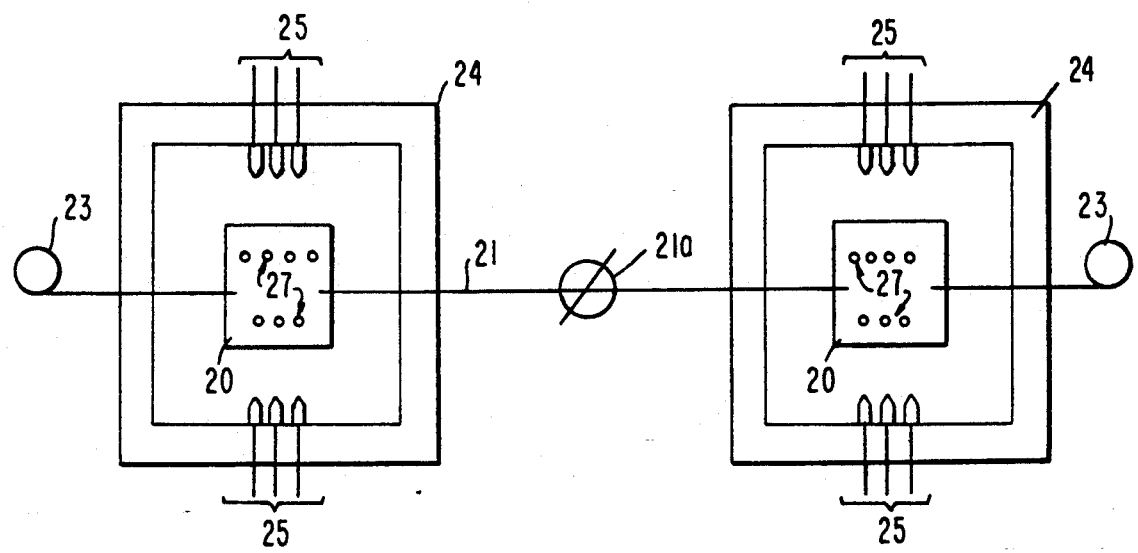
FIG. 2 is a schematic cross-section through a pair of the reactors in one reaction train of the apparatus of FIG. 1.

The pair of reactors 20 in one of the reaction trains is schematically shown in FIG. 2. Each reactor 20 may be of any suitable configuration and construction. An especially preferred configuration is a rectangular box of approximately 2.9 m×2.9 m×6.1 m. The reactor must be capable of withstanding an internal pressure of from about 25.4–607/mm Hg absolute and an internal temperature of from about 127.7°–440° C. A preferred material of construction is steel. An especially preferred material of construction for the reactor is ribbed reinforced steel.

After the rack 22 is loaded into the reactor 20, the reactor is sealed. The reactor may be sealed by bolting a reactor door shut. Preferable means for sealing the reactor 20 include a double sealing system wherein the reactor door is provided with a primary and a secondary gasket. In especially preferred sealing means a double sealing system is further provided with a multiplicity of stainless steel rods that are operated by compressed air cylinders so that said rods act against the door to make the seal even stronger. A pressure is then drawn in the reactor 20 resulting in an internal pressure of approximately 25.4–759 mm Hg absolute. The pressure may be drawn by pressure reducing means known in the art, such as by a vacuum pump 23.

An important aspect of the present invention is that the reactor 20 is sealed and does not allow significant amounts of air leakage. For the purposes of the present invention, the allowable ("minimal") amount of air leakage per hour is an average of less than about 3-weight percent air as compared to all vapors and gases in the reactor, preferably less than about 1.5 weight percent, and especially preferably less than about 0.5 weight percent. In yet more preferred embodiments air leakage is less than about 0.05 weight percent or even about 0 weight percent. An absence of oxygen in the reactor 20 is defined as an amount of oxygen that results when the average amount of air entering the reactor per hour is less than about 3 weight percent as compared to all vapors and gases in the reactor; preferably less than about 1.5 weight percent; especially preferably less than about 0.5 weight percent; and in yet more preferred embodiments less than about 0.05 weight percent or even about 0 weight percent.

As illustrated in FIG. 2, the reactor 20 is situated within insulated heating chamber 24. The chamber may be of any suitable configuration depending upon the configuration of the reactor, preferably a rectangular box with inside dimensions of approximately 5.0 m ×5.0 m×8.2 m. In a preferred embodiment, the reactor is situated within the heating chamber so that there is approximately 1.1 m of space between the reactor walls and the heating chamber walls on each side.

The chamber contains burners 25 to heat the contents of the reactor. In a preferred embodiment three burners are located under the reactor approximately 0.5 m above the chamber floor and three burners are located above the reactor approximately 0.5 m below the chamber ceiling. The burners may be fueled by methane or the like. In a preferred embodiment, a blower system introduces an air/fuel mixture fuel lines 26 (FIG. 1) to the burners of approximately 70% air and 30% methane. In an especially preferred embodiment, the burners are fueled by products of the process of the present invention, such as gaseous hydrocarbons. In especially preferred embodiments, the burners are fueled only by products of the process of the present invention and require no outside fuel source.

The burners are ignited and the reactor is heated. It is believed that natural convection heating of the tires occurs within the reactor although the present invention should not be limited thereto. The reactor and its contents are heated to a temperature of from about 127°–440° C., preferably from about 400–440° C; especially preferably about 420°–432° C., even more preferably from about 430°–432° C., and yet even more preferably approximately 432° C. Although not limiting the invention, it is believed to be important that the internal temperature not rise above 432° C. for a prolonged period of time because above 432° C. the sulfur in the rubber will gasify. Heating continues for a reaction time of approximately 1-5 hours, preferably about 2.5–4 hours, and especially preferably about 3–3½ hours. Reaction time for the purposes of this application means the amount of time that the rubber is heated.

As a result of the heating at subatmospheric pressures, the rubber dissociates into a vapor phase and a solid phase. For the purposes of the present invention, "dissociate" is not limited to any particular chemical reaction or phenomenon. However, it is believed that pyrolysis occurs during the process of the present invention.

The hydrocarbon vapors are removed from the reactor during heating. In a preferred embodiment, seven pipes 27 exit the reactor and pass through the heating chamber. Four of the pipes are evenly spaced 0.3 m above the vertical center of the reactor, and the remaining three pipes are evenly spaced 0.15 m above the floor of the reactor.

The internal pressure of the reactor generally rises during the operation, but should generally be less than 759 mm Hg absolute. During heating the internal pressure of the reactor may be about 25.4–759 mm Hg absolute, preferably about 316–625, mm Hg absolute; more preferably about 366–618 mm Hg absolute and even more preferably 416–568 mm Hg absolute. Heating continues and vapors are removed until the internal pressure stops increasing.

At least some of the hydrocarbon vapors are condensed to produce various types of liquid hydrocarbons. In a preferred embodiment, the seven pipes carry the hydrocarbon vapors out of the reactor, through exit lines 29, and into a 6.1 m long cooling trough 29 to condense some of the vapors. The pipes may then carry the hydrocarbon vapors through a second cooling trough. At the end of the cooling trough the pipes enter a collection container 30 where a liquid fuel is collected.

The fuel may then be stored in storage tank 31. This fuel is generally comparable to #4 fuel oil.

The liquid fuel has a low sulfur content. For the purposes of the present invention, a "low sulfur content" for liquid hydrocarbons is less than about 1.5 weight percent, preferably less than about 1.0 weight percent, especially preferably less than about 0.9 weight percent, and even more preferably less than 0.40 weight percent sulfur. Yet more preferred are liquid hydrocarbons having less than about 0.35 weight percent sulfur.

Approximately 90 weight percent of the vapors are typically condensed in the cooling trough 29, although this amount may vary. The non-condensed vapors may pass through further condensation means, such as one or more condensation towers 32. In a preferred embodiment the remaining vapors pass through a series of two condensation towers, each with secondary condensation units at the top. A heavy oil is collected from the first tower, and a lighter hydrocarbon (comparable to naphtha) is collected from the second tower.

The non-condensed vapors exit the second condensation tower and are collected as a gaseous fuel source. This stream typically comprises methane with small amounts of propane and butane. The vapors may be compressed and stored in storage tanks 33. A portion of the compressed vapors may then be removed through line 34 as a product fuel. A further portion of the compressed vapors may be removed from storage tanks 33, recycled through line 35, and fed through lines 26, and as a fuel source for the heating chamber burners.

Following the completion of the reaction the reactor is generally cooled. This can be achieved by introducing liquid nitrogen into the reactor.

The rack may be removed from the reactor by forklift. The solid phase remaining in the trays will generally contain a coke-like material and steel. This mixture can be processed using techniques known in the art to separate the steel from the coke-like material.

Figure 3:
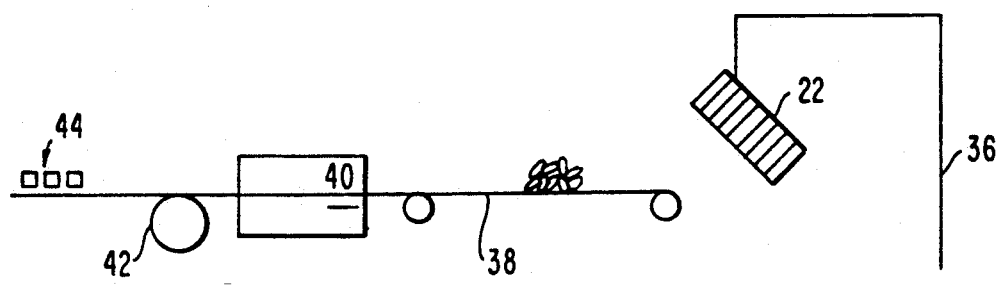
FIG. 3 is a schematic drawing of a preferred embodiment of the apparatus for processing the solid phase remaining after processing rubber tires in the reaction trains illustrated in FIG. 1.

As illustrated in FIG. 3 of the drawing, in a preferred embodiment the solid phase is processed as follows: First, the rack 22 is taken to a hoist 36. The hoist tips the trays so that the solid material falls onto a conveyor 38. The conveyor carries the material to a sealed chamber. The material passes through a magnetic conveyor separator 40 to remove relatively large pieces of steel, and then to an enclosed magnetic roller 42 to remove steel particles as small as 100 microns. The resulting product 44 is carbon black which is then boxed for shipment.

For the purposes of the present invention, a "solid carbonaceous material" comprises activated carbon and/or carbon black. Activated carbon is defined as a carbonaceous material with improved absorptive properties. Carbon black is defined as any of various black substances, consisting chiefly of carbon, that is used especially as pigments.

The solid carbonaceous material has a very low moisture level. Typically, it will comprise from about 85-93 weight percent carbon, from about 15-7 weight percent ash and less than 0.05 weight percent water. In an especially preferred embodiment, the activated carbon will comprise about 92% carbon, 8% ash and 0.003% water. These percentages will vary depending upon operating conditions.

In preferred embodiments, semi-steady state operation is achieved by cycling two reactors. Energy can also be conserved by using the waste heat from one reactor to pre-heat a second reactor.

In such preferred embodiments, the second reactor and heating chamber will generally have the same dimensions as the first reactor and heating chamber. While a reaction is occurring in the first reactor, the second reactor is loaded and sealed. The burner exhaust from the first heating chamber is allowed to pre-heat the second reactor.

The first and second reactors can be connected by a valved pressure equalization line 21. During the heating of the first reactor this line is normally shut by valve 21a. When heating has stopped in the first reactor, the pressure, of the second reactor is drawn approximately 457 mm Hg, resulting in an internal pressure, in the second reactor of approximately 303 Hg absolute. Valve 21a in the pressure equalization line is then opened so that the pressure is equalized in both reactors at about 505 mm Hg absolute. As a result heat passes from the first reactor to the second reactor and the temperature of the first reactor decreases while the temperature of the second reactor increases. Energy is therefore conserved.

Burners are then ignited in the second heating chamber, and heating begins in the second reactor. Vapors are condensed, and activated carbon is recovered, as described above.

The raw material for the process of the present invention will generally be used rubber tires, however, any type of rubber or organic material may be used. For the purposes of the present invention "rubber" shall include but not be limited to used tires and other materials such as butyl, neoprene and other waste rubbers. A typical used tire composition is presented in Roy (U.S. Pat. No. 4,740,270):

C: 85.7%
H: 7.5%
N: 0.3
O: 5.1%
S: 1.4%
Volatile matter: 65.2%
Fixed Carbon: 28.7%
Ashes: 6.1%
Calorific Value: 8,787 kcal kg$^{-1}$ An advantage of the present invention is that a profit can generally be made simply by accepting the raw materials. At present, the tipping fee charge for receiving used tires is approximately $0.15 per pound. The average waste passenger tire weighs approximately 22 lbs., therefore each passenger tire generates approximately $0.33 in cash flow. Truck and heavy equipment tires are much heavier and therefore produce more money for their receipt.

The apparatus of the present invention can be conveniently located at the source of raw materials. For instance, many landfills presently contain thousands or millions of tires and the apparatus can be located in the vicinity of such a landfill so that the tires can be easily acquired for use in the process in the apparatus.

As discussed above, several products are produced by the present invention, such as fuel oil, methane gas, carbon, and steel.

Typically 47 weight percent is reclaimed as fuel oil, equal to approximately 1.5 gallons of fuel oil per passenger tire. Uses for such a fuel oil include all uses of standard industrial fuels. Power plants can use the fuel as a pre-treatment for coal, as an ignitor for coal, or as a primary fuel for firing their boilers. Small power plants that use diesel generators can also use the fuel instead of or in conjunction with diesel fuel. The fuel may also be used as a home heating oil.

The gaseous hydrocarbons will comprise mostly methane gas. The methane gas can be used to fuel the burners of the present invention, or it can be sold as a fuel source. Optionally, methane can be used to generate electricity and the electricity can be sold, or the gaseous hydrocarbon can be used to fuel a co-generation unit so that steam and/or electricity can be sold.

The solid carbonaceous material that is a product of the present invention makes up approximately 43% by weight of the original used tires. The process will generally reclaim the carbon in the form of carbon black with a moisture content below 1%. Although not limiting the present invention, it is believed that the strengtheners added by tire manufacturers to the tires causes the carbon to become activated carbon black during processing. As a result, the carbon molecules are much stronger than the original carbon molecules and the carbon and the fuel oil will have a memory that causes them to recombine much easier as an emulsion.

There are many uses for the solid carbonaceous product of the present invention. It can be used in (a) roof coatings; (b) asphalt; (c) low pressure hoses such as those used in the automobile industry; (d) paints as fillers and as bonding agents; (e) plastics as fillers and as bonding agents; (f) ink; (h) waste treatment filters; (i) off road tires; and (j) marine coatings for use on docks, bridges, boats, etc.

The fuel oil and solid carbonaceous product can be combined to produce an emulsion for use in rubber/asphalt mixes. Rubber/asphalt highways have been built in several locations around the United States and these roads have proven to be superior than conventional asphalt roads. Until recently, the only form of rubber available for use in rubber/asphalt roads was crumb rubber which is produced by grinding tires in small particles. Crumb rubber often has all the steel and fiber normally found in tires contained within it. To process these particles, an adhesive must generally be added to bond the crumb rubber to the asphalt. It must then be heated to a high temperature in order to melt the rubber into the asphalt and form a rubbery goo. Problems generally occur throughout the application process. The steel and fibers clog small jets in the spray equipment and this requires frequent down time and expensive repairs at the job site. The cost of crumb rubber varies widely but it is generally much more costly than traditional asphalt.

Although not limiting the present invention, it is believed that the emulsion of the present invention is the result of the memory between the fuel oil and the carbon black that causes them to develop a strong bond very quickly. The emulsion has a high viscosity and contains fine carbon powders and can be easily mixed with asphalt using the same process currently used for mass produced emulsions with no special procedures being required at the job site.

The finished rubber/asphalt roadway is stronger, more flexible, and more weather resistant than traditional roadways. Also, traction is better and the roadway is quieter. Most importantly, the emulsion is less expensive than the crumb rubber which is presently used in such rubber/asphalt roads.

Emulsions may comprise from 10-15 weight percent activated carbon and from 15-20 weight percent fuel oil. Preferred emulsions comprise 30-35 weight percent activated carbon and 40-45 weight percent fuel oil, and especially preferred emulsions comprise about 45 weight percent activated carbon and about 55 weight percent fuel oil. Additional materials may also be included in the emulsions, such as sand, dirt, clay and tar.

Another product that is produced by the present invention is steel. Steel typically makes up approximately 4% by weight of each tire. The steel can be recovered and easily sold to local scrap metal markets.

In preferred embodiments of the present invention, approximately 100 percent of the used tires are reclaimed with no secondary waste and minimal air pollution emissions. In fact it is another significant advantage of the present invention that very little air pollution is produced. Minimal amounts of air pollution is defined herein as meaning that a process or apparatus consuming 46,800 tons of tires per year will produce less than the following amounts of emissions per year:

| Particulate Matter (including condensables) | 15 tons |
|---|---|
| Sulfur Dioxide | 0.2 tons |
| Nitrogen Oxide | 0.9 tons |
| Carbon Monoxide | 2.2 tons |

In preferred embodiments, the processes and apparatuses of the present invention will produce de minimis amounts of emissions. For the purposes of the present invention, de minimis emissions is defined as meaning that a process or apparatus consuming 46,800 tons of tires per year will produce less than the following amounts of emissions per year:

| Particulate matter including condensables) | 1.24 tons |
|---|---|
| Sulfur Oxides | 0.94 tons |
| Nitrogen Oxides | 0.002 tons |
| Carbon Monoxide | 13.368 tons |
| Beryllium | $4.000 \times 10^{-5}$ |
| Lead | $5.200 \times 10^{-4}$ |
| Mercury | $2.000 \times 10^{-6}$ |

EXAMPLE 1

10,000 pounds of used automobile tires were reduced to six non-uniform pieces and loaded into racks. Each rack had six trays spaced on a vertical axis approximately 0.3 m apart from each other.

The racks were loaded into a reactor having a volume of approximately 65.1 m³, and the reactor was sealed. A vacuum of 416 mm Hg was drawn, and air leakage was maintained so that an average of less than 0.5 weight percent air entered the reactor per hour as compared to all vapors and gases in the reactor. Burners were ignited and heating of the reactor began. The internal temperature of the reactor was allowed to increase until a temperature of 432° C. was reached. This temperature was maintained for three hours.

Air emissions were monitored throughout the operation. All emissions exited through a single point source consisting of a 0.3 m diameter stack. There were no emission controls on the combustion gases used in the process other than the use of efficient burners to allow sufficient mixing, temperature and residence time. The gases discharged to rectangular horizontal ductwork for approximately 12 m and then turned 90 degrees to the vertical 0.3 m diameter stack through the roof. The test ports were installed at three locations along the ductwork and stack.

The following Tables 1-3 summarize the air emissions:

TABLE 1
Summary of Criteria Pollutants Test Results

| Pollutant | Test Method | Regulated Emissions Actual Emmissions | Regulated Allowable | Annual Emission Rates Actual Emissions (tpy) | DeMinimis Rate (tpy) |
|---|---|---|---|---|---|
| Particulates | 5 | 0.03049 Lb/hr | 2.3 lb/hr | 0.05488 | 25 |
| Sulfur dioxide | 6 | 7.88E-05 lb/mmbtu | 8.0 lb/mmbtu | 0.10364 | 40 |
| Nitrogen Oxides | 7 | 0.00007 lb/h4 | not regulated | 0.00013 | 40 |
| Carbon Monoxide | 10 | 0.763 lb/hr | not regulated | 0.714 | 100 |
| Beryllium | MM-MM5 | 2.95E-06 lb/hr | not regulated | 2.76E-06 | 0.0004 |
| Lead | MM-MM5 | 2.95E-05 lb/hr | not regulated | 2.76E-05 | 0.6 |
| Mercury | MM-MM5 | 1.15E-07 lb/hr | not regulated | 1.08E-07 | 0.1 |

Abbreviations
lb/hr = pounds of emissions per hour of combustion operation
lb/mmbtu = pounds of emissions per million Btu heat input
MM-MM5 = multiple metals using modified method 5 sample train
tpy = tons per year
Annual emissions are based on:
3 hours of combustion per batch/2 batch operations per day
6 operating days per week/52 weeks per year

TABLE 2
Summary of Condensable Emissions and Metals Test Results

| Pollutant | Test Method | Average Emissions (gr/dscf) | (lb/hr) | (tpy) |
|---|---|---|---|---|
| Condensable Emissions | 5 | 0.01109 | 0.04033 | 0.0363 |
| Antimony | MM-MM5 | 6.27E-07 | 2.32E-06 | 2.18E-06 |
| Arsenic | MM-MM5 | 4.26E-07 | 2.37E-06 | 2.22E-06 |
| Cadmium | MM-MM5 | 7.92E-07 | 2.95E-06 | 2.76E-06 |
| Chromium | MM-MM5 | 1.40E-06 | 5.23E-06 | 4.89E-06 |
| Cobalt | MM-MM5 | 1.77E-06 | 6.61E-06 | 6.18E-06 |
| Manganese | MM-MM5 | 2.07E-05 | 7.70E-05 | 7.21E-05 |
| Nickel | MM-MM5 | 5.37E-05 | 5.91E-04 | 5.53E-04 |
| Selenium | MM-MM5 | 4.44E-06 | 1.64E-05 | 1.54E-05 |
| Zinc | MM-MM5 | 5.75E-06 | 2.14E-05 | 2.00E-05 |

Annual emissions are based on:
3 hours of combustion per batch/2 batch operations per day
6 operating days per week/52 weeks per year
tpy = tons per year

TABLE 3
Summary of Volatile Organic Compound Pollutants Test Results Based on Volatile Organic Sampling Train (VOST)

| Pollutant | Molecular Weight (AMU) | Ave. Amount Collected (ng/20 liter) | Average Emissions (ppm) | (gr/dscf) | (lb/hr) | (tpy) |
|---|---|---|---|---|---|---|
| Benzene | 78 | 17,300 | 0.282 | 3.78E-4 | 1.13E-3 | 1.24E-3 |
| Napthalene | 128 | <20 | <0.0000199 | <4.37E-7 | <1.59E-6 | <1.43E-6 |
| Butadiene | 54 | <20 | <0.0000471 | <4.37E-7 | <1.59E-6 | <1.43E-6 |
| Ethyl Benzene | 106 | 1,056 | 0.0127 | 3.78E-4 | 1.38E-3 | 1.24E-3 |
| Phenol | 94 | <20 | <0.0000271 | <4.37E-7 | <1.59E-6 | <1.43E-6 |
| Top Five Peaks: | | | | | | |
| Hexamethyldisiloxane | 162 | 56,333 | 0.443 | 1.23E-3 | 4.48E-3 | 4.03E-3 |
| Octamethyltrisiloxane | 236 | 8,833 | 0.0477 | 1.93E-4 | 7.03E-4 | 6.32E-4 |
| Trimethylsilanol | 90 | 19,333 | 0.274 | 4.22E-4 | 1.54E-3 | 1.38E-3 |
| Toluene | 92 | 8,567 | 0.119 | 1.87E-4 | 6.81E-4 | 6.13E-4 |
| 2-Methylcyclopentanone | 98 | 2,367 | 0.0308 | 5.17E-5 | 1.88E-4 | 1.69E-4 |
| 2-Propyn-1-ol* | 56 | 46,667 | 1.06 | 1.02E-3 | 3.71E-3 | 3.34E-3 |
| 1-Propene* | 42 | 10,333 | 0.314 | 2.26E-4 | 8.22E-4 | 7.40E-4 |
| Methyl Butene Isomer | 70 | 9,000 | 0.164 | 1.97E-4 | 7.16E-4 | 6.44E-4 |
| 2-Methyl-1-propene | 56 | 5,000 | 0.114 | 1.09E-4 | 3.98E-4 | 3.58E-4 |

Notes:
*Best Computer Match
annual emissions are based on:
3 hours of combustion per batch/2 batch operations per day
6 operating days per week/52 weeks per year
tpy = tons per year The rubber dissociated into a solid and vapor phase. Some of the vapor phase was condensed to produce a fuel oil and remaining gaseous hydrocarbon. The fuel oil was analyzed. The results of the analysis are shown below in Table 4:

TABLE 4

| | |
|---|---|
| Appearance as received | Dark, Clear |
| Color, ASTM | >8.0 |
| Water | Trace |
| Gravity, degrees A.P.I. at 60° F. | 20.1 |
| Viscosity, S.S.U. at 100° F. | 47.4 |
| Flash Point | 80° F. |
| Sulfur | 0.34% |
| Cloud Point | Too dark in color to determine |
| Pour Point | Below −40° F. |
| Carbon residue on 12.5% distillation bottoms | 8.56% |
| Corrosion test, copper strip, ASTM D-130, 212° F., 3 hours | ASTM 1A, Slight Tarnish |
| Filerable Solids, 0.8 micron, mg/gal | 2835 |
| Ash on filterable solids | 1.07% |
| Heat Content, BTU per gallon | 143,174 |
| Distillation | |
| Initial boiling point | 270° F. |

TABLE 4-continued

| | |
|---|---|
| 10% over at | 333° F. |
| 50% over at | 586° F. |
| End Point | 669° F. |
| Recovery | 87.5% |
| Residue and loss | 12.5% |
| Distillation range | 399° F. |

The gaseous hydrocarbon product of the present invention was analyzed by gas chromatography-mass spectrometry. A minimum of thirty (30) components were eluted from the chromatograph. Additional components may have co-eluted within the same peak.

Comparisons of mass spectra of each eluted peak with spectra stored in a library provided a list of best possible matches for each peak. The most common components were derivatives of (a) three carbon chains, e.g., propane and propene; (b) four carbon chains, e.g., butane and butene; and (c) cyclic aromatic by diocarbons, e.g., benzene, xylene, toluene, and dichlorobenzene. Group (c) is common of gasoline products.

All of the gaseous hydrocarbon compounds were flammable and would burn in the combustion heaters of an autoclave.

The solid phase was processed to form a solid carbonaceous product which was also analyzed. The results of the analysis are shown below in Table 5:

TABLE 5

| | As received | Dry Basis |
|---|---|---|
| Moisture | 0.90% | |
| Ash | 8.41% | 8.49% |
| Carbon | 85.93 | 86.75% |
| BTU/lb | 13,587 | 13,710 |

The ash was analyzed and found to contain the following in weight percent:

| | |
|---|---|
| Aluminum | 1.50 |
| Chromium | 0.13 |
| Iron | 1.10 |
| Lead | 0.18 |
| Barium | 0.25 |
| Magnesium | 1.50 |
| Phosphorous | 0.80 |
| Potassium | 0.32 |
| Silicon Dioxide | 19.09 |
| Zinc | 52.33 |
| Titanium Dioxide | 14.27 |
| Calcium Oxide | 5.06 |

-continued

| | |
|---|---|
| Sulfur | 2.77 |

The foregoing description and examples illustrate selected embodiments of the present invention and in light thereof variations and modifications will be suggested to those skilled in the art, all of which are within the spirit and purview of this invention

I claim:

1. An apparatus for producing liquid and gaseous hydrocarbons and solid carbonaceous materials from rubber, said apparatus comprising:
   (a) two sealed reactors for holding the rubber, said reactors capable of withstanding internal temperatures of from about 127–440° C. and internal pressures of from about 25.4–759 mm Hg absolute with minimal amounts of air leakage;
   (b) valved pressure equalization means capable of equalizing the pressure between the two sealed reactors;
   (c) heating means for heating the two sealed reactors to an internal temperature of from about 127°–440° C. and pressure reducing means for producing a pressure in the two sealed reactors of from about 25.4–759 mm Hg so that any rubber in the reactors dissociates into a vapor phase and a liquid phase;
   (d) means for withdrawing the vapor phase from the two reactors and delivering it to a condensing means;
   (e) condensing means for condensing at least some of the vapor phase to produce low sulfur liquid hydrocarbons and remaining gaseous hydrocarbons; and
   (f) processing means for processing the solid phase to produce solid carbonaceous materials.

2. An apparatus as defined in claim 1 wherein the valved pressure equalization means comprises a valved pipe running between the two sealed reactors that allows pressure equalization between the two reactors when the valve is open and thereby allows heat to pass from one reactor to the other reactor.

3. An apparatus as defined in claim 2 wherein the rubber comprises whole rubber tires.

4. An apparatus as defined in claim 3 further comprising
   (g) means for delivering at least some of the remaining gaseous hydrocarbons to the heating means to serve as a fuel for the heating means.

* * * * *